US009046494B2

(12) United States Patent
Song et al.

(10) Patent No.: US 9,046,494 B2
(45) Date of Patent: Jun. 2, 2015

(54) OPTICAL SENSING SYSTEM AND A METHOD OF DETERMINING A CHANGE IN AN EFFECTIVE REFRACTIVE INDEX OF A RESONATOR OF AN OPTICAL SENSING SYSTEM

(75) Inventors: Junfeng Song, Singapore (SG); Xianshu Luo, Singapore (SG); Qing Fang, Singapore (SG); Mingbin Yu, Singapore (SG); Guo Qiang Patrick Lo, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 697 days.

(21) Appl. No.: 13/338,693

(22) Filed: Dec. 28, 2011

(65) Prior Publication Data
US 2012/0194803 A1 Aug. 2, 2012

(30) Foreign Application Priority Data

Dec. 28, 2010 (SG) ............................... 201009654-3

(51) Int. Cl.
| | |
|---|---|
| *G01N 21/41* | (2006.01) |
| *H01S 3/10* | (2006.01) |
| *G01N 21/77* | (2006.01) |
| *G02B 6/293* | (2006.01) |
| *H01S 5/14* | (2006.01) |
| *H01S 5/026* | (2006.01) |
| *G01N 21/45* | (2006.01) |

(52) U.S. Cl.
CPC ............ *G01N 21/7746* (2013.01); *H01S 5/141* (2013.01); *H01S 5/026* (2013.01); *G01N 21/41* (2013.01); *G01N 2021/458* (2013.01); *G02B 6/29341* (2013.01)

(58) Field of Classification Search
USPC .................... 356/128; 385/129, 131, 146, 27; 250/227.4, 492.3; 372/20
See application file for complete search history.

(56) References Cited

U.S. PATENT DOCUMENTS 7,062,118 B2     6/2006  Chiu et al.
7,145,660 B2 *  12/2006  Margalit et al. ............... 356/477
(Continued)

OTHER PUBLICATIONS

F.S. Tan, et al., High ON_OFF Ratio of Cascaded Two and Three Microring Resonators Based on SiON Technology for Bandpass Filter Applications, ECOC-IOOC, Rimini, Italy, 2003—utwente.nl.
(Continued)

*Primary Examiner* — Sang Nguyen
(74) *Attorney, Agent, or Firm* — K. David Crockett, Esq.; Niky Economy Syrengelas, Esq.; Crockett & Crockett, PC

(57) ABSTRACT

According to embodiments of the present invention, an optical sensing system is provided. The optical sensing system includes a resonator arrangement including a first resonator, wherein an effective refractive index of the first resonator is changeable in response to a change in a refractive index of a cladding of the first resonator, and a second resonator to which a current or voltage being adjustable in response to a change in the effective refractive index of the first resonator is applied, wherein the optical sensing system is configured to determine the change in the effective refractive index of the first resonator based on a change in the current or voltage applied to the second resonator. Further embodiments provide a method of determining a change in an effective refractive index of a resonator of an optical sensing system.

21 Claims, 10 Drawing Sheets

(56) References Cited

U.S. PATENT DOCUMENTS

| | | | |
|---|---|---|---|
| 7,231,113 | B2 | 6/2007 | Chu et al. |
| 7,356,221 | B2 | 4/2008 | Chu et al. |
| 7,512,298 | B2 | 3/2009 | Yi et al. |
| 7,796,262 | B1 | 9/2010 | Wang et al. |
| 2004/0114899 | A1* | 6/2004 | Mattsson ................. 385/129 |
| 2004/0146431 | A1 | 7/2004 | Scherer et al. |
| 2004/0165565 | A1* | 8/2004 | Omae et al. ............... 370/338 |
| 2006/0170931 | A1 | 8/2006 | Guo et al. |
| 2008/0123701 | A1* | 5/2008 | He ............................ 372/23 |
| 2009/0046748 | A1* | 2/2009 | Kato ......................... 372/20 |
| 2009/0122817 | A1* | 5/2009 | Sato et al. ................. 372/20 |
| 2009/0154505 | A1* | 6/2009 | Oh et al. ................... 372/20 |
| 2009/0291446 | A1* | 11/2009 | Samadpour ................. 435/6 |
| 2010/0209038 | A1* | 8/2010 | Popovic et al. .............. 385/1 |
| 2011/0194572 | A1* | 8/2011 | Yamazaki et al. ........... 372/6 |
| 2012/0298849 | A1* | 11/2012 | He et al. ................ 250/227.14 |

OTHER PUBLICATIONS

O. Schwelb, et al., Parallel-Coupled Phase-Matched Multiring Optical Filters, Microwave and Optical Technology Letters, V44, Issue 6, p. 536.

K. De Vos, et al., Silicon-on-Insulator Microring Resonator for Sensitive and Label-Free Biosensing, Opt. Express 15, pp. 7610-7615 (2008).

D. Xu, et al. Folded Cavity SOI Microring Sensors for High Sensitivity and Real Time Measurement of Biomolecular Binding, Opt. Express 16, pp. 15137-15148 (2008).

M. Iqbal, et al., Label-Free Biosensor Arrays Based on Silicon Ring Resonators and High-Speed Optical Scanning Instrumentation, IEEE J. Select. Top. Quantum Electron. 16, pp. 654-661 (2010).

T. Claes, et al., Label-Free Biosensing with a Slot-Waveguide-Based Ring Resonator in Silicon on Insulator, J. Photon. 1, pp. 197-204 (2008).

J. Song, et al. Fast and Low Power Michelson Interferometer Thermo-Optical Switch on SOI, Opt. Express 16, pp. 15304-15311 (2008).

X. Fan, et al., Sensitive Optical Biosensors for Unlabeled Targets: A Review, Anal. Chim. Acta 620, pp. 8-26 (2008).

D. Dai, Highly Sensitive Digital Optical Sensor Based on Cascaded High-Q Ring-Resonators, Opt. Express 17, pp. 23817-23822 (2009).

T. Claes, et al., Experimental Characterization of a Silicon Photonic Biosensor Consisting of Two Cascaded Ring Resonators based on the Vernier-Effect and Introduction of a Curve Fitting Method for an Improved Detection Limit, Opt. Express 18, pp. 22747-22761 (2010).

A. Ksendzov, et al., Integrated Optics Ring Resonator Sensors for Protein Detection, Opt. Lett. vol. 30, pp. 3344-3346 (CalTec) (2005).

A. Yalcin, et al. Optical Sensing of Biomolecules Using Microring Resonators, IEEE J. Select. Top. Quantum Electron. vol. 12, pp. 148-154 (Boston University) (2006).

M. Iqbal, et al., Label-Free Biosensor Arrays Based on Silicon Ring Resonators and High-Speed Optical Scanning Instrumentation, IEEE J. Select. Top. Quantum Electron. vol. 16, pp. 654-661 (Genalyte, Inc., San Diego) (2010).

D. Xu, et al., Label-Free Biosensor Array Based on Silicon-on-Insulator Ring Resonators Addressed Using a WDM Approach, Opt. Lett. vol. 35, pp. 2771-2773 (IMS, NRCC) (2010).

X. Luo, A Serial Cascaded Double-Microring-Based Silicon Photonic Circuit for High-Speed On-Chip Clock-Recovery Applications, Group IV Photonics, 2009. GFP '09. 6th IEEE International Conference on.

C. Li, et al., Dual-Microring-Resonator Electro-Optic Logic Switches on a Silicon Chip, Semiconductor Science and Technology V23, 064010, 2008.

* cited by examiner

United States Patent 9,046,494 B2

OPTICAL SENSING SYSTEM AND A METHOD OF DETERMINING A CHANGE IN AN EFFECTIVE REFRACTIVE INDEX OF A RESONATOR OF AN OPTICAL SENSING SYSTEM

CROSS-REFERENCE TO RELATED APPLICATION

This application claims the benefit of priority of Singapore patent application No. 201009654-3, filed 28 Dec. 2010, the content of it being hereby incorporated by reference in its entirety for all purposes.

TECHNICAL FIELD

Various embodiments relate to an optical sensing system and a method of determining a change in an effective refractive index of a resonator of an optical sensing system.

BACKGROUND

Label-free optical biological/chemical sensors are essential in the application of medical diagnosis, healthcare and environmental monitoring, amongst others. Among all the approaches, silicon optical microresonator-based biosensors are regarded to be very promising due to their high sensitivity to refractive index change ($\sim 10^{-4}$-$10^{-7}$ RIU (refractive index unit)), comparable to the conventional surface plasmon resonance (SPR) technique sensitivity), compact footprint ($\sim$10's μm-$\sim$100 μm), and potential large-scale-integration with microfluidics.

Single microring resonator-based biosensors in silicon-on-insulator (SOI) have been demonstrated using either conventional microrings [K. De Vos, et al., *Opt. Express* 15, pp. 7610-7615 (2008); D. Xu, et al., *Opt. Express* 16, pp 15137-15148 (2008); M. Iqbal, et al., *IEEE J. Select. Top. Quantum Electron.* 16, pp. 654-661 (2010).] or slot-waveguide microring [T. Claes, et al., *J. Photon.* 1, pp. 197-204 (2008).]. The demonstrated detection limit ranges from $10^{-5}$-$10^{-7}$ RIU.

However, for nearly all the demonstrated microresonator sensors, the wavelength-scanning method using wavelength-tunable lasers was considered to be the "default" technique for measuring sharp resonance wavelength shift. The wavelength-scanning method requires high-resolution wavelength tunable lasers in order to measure the sharp resonance wavelength shift, in which the detection limit is limited by the laser resolution. Furthermore, high-resolution wavelength-scanning lasers are very expensive and not suitable for point-of-care applications.

SUMMARY

According to an embodiment, an optical sensing system is provided. The optical sensing system may include a resonator arrangement including a first resonator, wherein an effective refractive index of the first resonator is changeable in response to a change in a refractive index of a cladding of the first resonator, and a second resonator to which a current or voltage being adjustable in response to a change in the effective refractive index of the first resonator is applied, wherein the optical sensing system is configured to determine the change in the effective refractive index of the first resonator based on a change in the current or voltage applied to the second resonator.

According to an embodiment, a method of determining a change in an effective refractive index of a resonator of an optical sensing system is provided. The method may include determining if an output light intensity measured by a detector of the optical sensing system is at a predefined value, if the measured output light intensity is not at the predefined value, adjusting a current or voltage applied to a further resonator of the optical sensing system to align an optical resonant frequency of the further resonator with an optical resonant frequency of the resonator until the measured output light intensity is at the predefined value, determining the change in the effective refractive index of the resonator based on the change in the current or voltage applied to the further resonator.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DETAILED DESCRIPTION

Figure 1A:
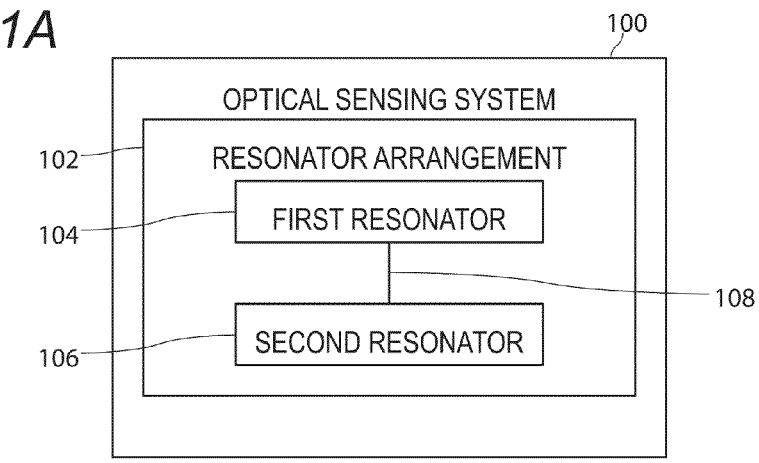
FIG. 1A shows a schematic block diagram of an optical sensing system, according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other method or device. Similarly, embodiments described in the context of a method are analogously valid for a device, and vice versa.

In the context of various embodiments, the phrase "at least substantially" may include "exactly" and a variance of +/−5% thereof. As an example and not limitations, "A is at least substantially same as B" may encompass embodiments where A is exactly the same as B, or where A may be within a variance of +/−5%, for example of a value, of B, or vice versa.

In the context of various embodiments, the term "about" or "approximately" as applied to a numeric value encompasses the exact value and a variance of +/−5% of the value.

As used herein, the term "and/or" includes any and all combinations of one or more of the associated listed items.

Various embodiments relate to the fields of silicon nano/micro-photonics and/or optical biological/chemical sensing.

Various embodiments provide an optical sensing system, for example a microring resonator-based optical sensor or sensing system. The optical sensing system may be a biological/chemical sensor. In various embodiments, the optical sensing system includes serial-cascaded dual-microring resonators, where one of the microring resonators serves as a sensing element while the other microring resonator serves as a tracing element. In other words, the optical sensing system of various embodiments is a dual-microring resonator-based optical sensing system, which may include identically designed add-drop microring resonators, where one microring resonator (e.g. sensing resonator or sensing element) may be used for sensing while the other microring resonator (e.g. tracing resonator or tracing element) may be used for tracing, for example for tracking or responding to any changes in the properties, e.g. effective refractive index, of the sensing resonator. The tracing resonator may be integrated with the sensing resonator and may function as a microring filter to determine the resonance wavelength shift of the sensing resonator. The optical sensing system of various embodiments may provide a Lorentz filter response.

In various embodiments, the sensing resonator may have an optical shift or change and the tracing resonator may be tuned, for example electrically tuned by applying a current or a voltage, to shift its optical properties so as to match the optical shift of the sensing resonator. The electrical tuning may result in an increased output signal detected. Based on the electrical tuning, the output signal level may then be converted to a sensing level. In other words, the sensing level may be determined as a function of the output signal level.

In various embodiments, the sensing resonator may sense a shift or change in its resonance wavelength due to a change in its effective refractive index, for example due to or in response to one or more stimuli, while the tracing resonator, which is tunable, traces the resonance wavelength shift due to the change in the effective refractive index of the sensing resonator. In various embodiments, the change in the effective refractive index of the sensing resonator may be due to a change in the refractive index of the cladding (e.g. upper cladding layer) of the sensing resonator. In various embodiments, by providing the tracing resonator and incorporating thermo-optical tuning or electro-optical tuning with the tracing resonator (e.g. the tracing resonator may be dynamically thermally tuned or electrically tuned, due to thermo-optic (TO) or electro-optic (EO) effect respectively, (e.g. free carrier dispersion effect, liquid crystal tuning, polymer tuning)), the resonance wavelength shift may be obtained or determined, for example, by directly reading or determining the current or voltage applied to the tracing resonator, and/or changes in the current or voltage applied. The current or voltage may be applied using a voltage/current supply source. For TO tuning, the tracing resonator includes a thermal heater, and the resonance wavelength shift may be obtained or determined, for example, by directly reading or determining the current or voltage applied to the thermal heater of the tracing resonator, and/or changes in the current or voltage applied.

In various embodiments of the optical sensing system, the sensing interrogation may be the detection of the maximum intensity (e.g. power), based on the filter-cascading effect of the sensing resonator and the tracing resonator.

The optical sensing system of various embodiments does not require the use of a wavelength-scanning method for sensing interrogation which requires advanced instruments and which are unsuitable for portable application, thereby providing cost-effective optical sensing (e.g. optical biological/chemical sensing) and potential point-of-care applications, e.g. biomedical applications. Therefore, the optical sensing system of various embodiments eliminates or does not require the usage of high-resolution wavelength-tunable lasers, thus significantly lowering the cost.

FIG. 1A shows a schematic block diagram of an optical sensing system 100, according to various embodiments. The optical sensing system 100 includes a resonator arrangement 102 including a first resonator 104, wherein an effective refractive index of the first resonator 104 is changeable in response to a change in a refractive index of a cladding (e.g. upper cladding) of the first resonator 104, and a second resonator 106 to which a current or voltage being adjustable in response to a change in the effective refractive index of the first resonator 104 is applied, wherein the optical sensing system 100 is configured to determine the change in the effective refractive index of the first resonator 104 based on a change in the current or voltage applied to the second resonator 106. In the context of various embodiments, the light may be broadband or wideband.

In other words, the refractive index of the cladding (e.g. the cladding or upper cladding of the first resonator 104 that may be exposed to a stimulus) of the first resonator 104 may change, for example in response to a stimulus, for example a sample or fluid which may come in contact with the cladding, e.g. for sensing applications. The change in the refractive index of the cladding of the first resonator 104 may result in a change in the effective refractive index of the first resonator 104. A current or a voltage may be applied to the second resonator 106, and the current or the voltage may be adjusted in response to the change in the effective refractive index of the first resonator 104. The optical sensing system 100 may then determine the change in the effective refractive index of the first resonator 104 based on a change in the current or voltage applied to the second resonator 106.

In FIG. 1A, the line represented as 108 is illustrated to show the relationship between the first resonator 104 and the second resonator 106, which may include electrical coupling and/or mechanical coupling and/or optical coupling.

Figure 1B:
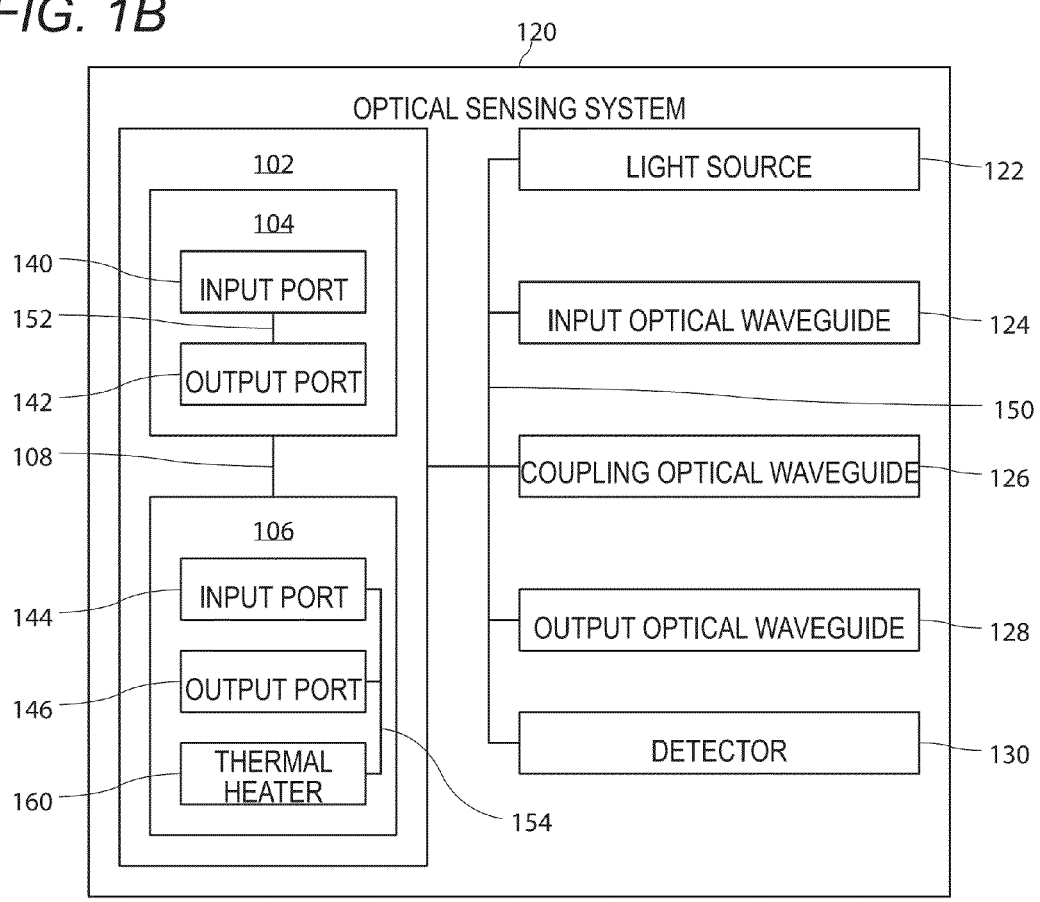
FIG. 1B shows a schematic block diagram of an optical sensing system, according to various embodiments.

FIG. 1B shows a schematic block diagram of an optical sensing system 120, according to various embodiments. The optical sensing system 120 includes a resonator arrangement 102 including a first resonator 104 and a second resonator 106, which may be similar to the embodiment as described in the context of FIG. 1A.

In various embodiments, the second resonator 106 includes a thermal heater 160, and wherein a current or voltage being adjustable in response to a change in the effective refractive index of the first resonator 104 is applied to the thermal heater 160, wherein the optical sensing system 120 is configured to determine the change in the effective refractive index of the first resonator 104 based on a change in the current or voltage applied to the second resonator 106 (i.e. a change in the current or voltage applied to the thermal heater 160). In various embodiments, the thermal heater 160 may be integrated with the second resonator 106. In various embodiments, the optical sensing system 120 may include a thermal heater configured to supply heat to the second resonator 106 (e.g. thermally coupled to the second resonator 106).

The optical sensing system 120 may further include a light source 122 configured to provide light. In the context of various embodiments, the light source 122 may be or may include a broadband light source, including but not limited to a white light source, a halogen lamp, a light emitting diode (LED) and a light source providing amplified spontaneous emission (ASE).

The optical sensing system 120 may further include an input optical waveguide 124 configured to guide received light, wherein the resonator arrangement 102 may be coupled to the input optical waveguide 124 to receive the light from the input optical waveguide 124. In various embodiments, the input optical waveguide 124 may be coupled, for example optically coupled and/or mechanically coupled, to the light source 122 to receive light from the light source 122 and guide the light to the resonator arrangement 102.

The optical sensing system 120 may further include a coupling optical waveguide 126 coupled between the first resonator 104 and the second resonator 106, the coupling optical waveguide 126 being configured to guide light received from the first resonator 104 to the second resonator 106 or from the second resonator 106 to the first resonator 104. Therefore, in various embodiments, the first resonator 104 is indirectly coupled to the second resonator 106, or vice versa, via the coupling optical waveguide 126.

In various embodiments, as the coupling optical waveguide 126 is coupled between the first resonator 104 and the second resonator 106, the first resonator 104 is indirectly coupled to the second resonator 106, or vice versa, via the coupling optical waveguide 126. As the first resonator 104 and the second resonator 106 are two different or separate structures, and which may be independent from each other, the first resonator 104 and the second resonator 106 have their respective spectral responses. By indirectly coupling the first resonator 104 and the second resonator 106 via the coupling optical waveguide 126, the tracing function (i.e. where one resonator may track the optical resonance shift of the other resonator) may be carried out.

The optical sensing system 120 may further include an output optical waveguide 128 coupled to the resonator arrangement 102, the output optical waveguide 128 being configured to output light received from the resonator arrangement 102.

The optical sensing system 120 may further include a detector 130 coupled to the output optical waveguide 128, wherein the detector 130 is configured to receive light from the output optical waveguide 128. In the context of various embodiments, the detector 130 may be or may include a photodetector, for example a silicon-germanium (SiGe) photodetector or a hybrid III-V-on-silicon photodetector. As used herein with respect to the photodetector, the term "III" refers to Group III elements (e.g. aluminum, gallium) and the term "V" refers to Group V elements (e.g. phosphorus, antimony).

The detector 130 may be configured to measure an intensity of light received from the output optical waveguide 128. In various embodiments, the intensity of light may be maximum when an optical resonant frequency of the first resonator 104 and an optical resonant frequency of the second resonator 106 are aligned. In other words, the intensity of light may be maximum when the optical resonant frequency (or resonant wavelength) of the first resonator 104 and the optical resonant frequency (or resonant wavelength) of the second resonator 106 are at least substantially same. In various embodiments, the optical resonant frequency of the first resonator 104 may change in response to the change in the effective refractive index of the first resonator 104. In various embodiments, the optical sensing system 120 may be configured to change the current or voltage applied to the second resonator 106 to align the optical resonant frequency of the second resonator 106 with the changed optical resonant frequency of the first resonator 104 such that the intensity of light measured by the detector 130 may be maximum.

In various embodiments, the first resonator 104 may be coupled to the input optical waveguide 124 and the coupling optical waveguide 126, and the second resonator 106 may be coupled to the output optical waveguide 128 and the coupling optical waveguide 126. The first resonator 104 may have an input port 140 coupled to the input optical waveguide 124 and an output port 142 coupled to the coupling optical waveguide 126, wherein the first resonator 104 may be configured to receive light from the input optical waveguide 124 via the input port 140, direct the light to the output port 142, and transmit the light to the coupling optical waveguide 126 via the output port 142. The second resonator 106 may have an input port 144 coupled to the coupling optical waveguide 126 and an output port 146 coupled to the output optical waveguide 128, wherein the second resonator 106 may be configured to receive light from the coupling optical waveguide 126 via the input port 144, direct light from the input port 144 to the output port 146, and transmit the light to the output optical waveguide 128 via the output port 146.

In various embodiments, the second resonator 106 may be coupled to the input optical waveguide 124 and the coupling optical waveguide 126, and the first resonator 104 may be coupled to the output optical waveguide 128 and the coupling optical waveguide 126. The second resonator 106 may have an input port 144 coupled to the input optical waveguide 124 and an output port 146 coupled to the coupling optical waveguide 126, wherein the second resonator 106 may be configured to receive light from the input optical waveguide 124 via the input port 144, direct the light to the output port 146, and transmit the light to the coupling optical waveguide 126 via the output port 146. The first resonator 104 may have an input port 140 coupled to the coupling optical waveguide 126 and an output port 142 coupled to the output optical waveguide 128, wherein the first resonator 104 may be configured to receive light from the coupling optical waveguide 126 via the input port 140, direct light from the input port 140 to the output port 142, and transmit the light to the output optical waveguide 128 via the output port 142.

In FIG. 1B, the lines represented as 150, 152, 154 are illustrated to show the relationship between the different features or components, which may include electrical coupling and/or mechanical coupling and/or optical coupling.

In the context of various embodiments, the first resonator 104 and the second resonator 106 may be identical. This means that the first resonator 104 and the second resonator 106 may have at least substantially similar or identical parameters, for example in terms of the structure, configuration, shape (e.g. ring-shaped, e.g. circular or elliptical) and dimensions (e.g. radius). In various embodiments, having identical or identically designed first resonator 104 and second resonator 106 may mean that the respective optical resonances, e.g. the respective resonant wavelengths (or resonant frequencies) of first resonator 104 and the second resonator 106 may be at least substantially aligned. The respective resonant wavelengths may be at least substantially aligned at the initial state of the optical sensing system 100 when not in operation, and the resonant wavelength of one of the resonators may be tuned, for example via electro-optic or thermo-optic effect, so as to at least substantially align with the resonant wavelength of the other resonator which may have shifted as a response to a stimulus during sensing operation.

In the context of various embodiments, each of the first resonator 104 and the second resonator 106 may include or may be a closed loop. Each closed loop may be ring-shaped, for example including circular or elliptical shapes. In various embodiments, each of the first resonator 104 and the second resonator 106 is a ring (e.g. microring) resonator or a microresonator. However, it should be appreciated that other resonators, including but not limited to microdisk and Fabry-Perot cavity/resonator may also be used for the first resonator 104 and/or the second resonator 106.

In the context of various embodiments, the first resonator 104 and the second resonator 106 may be independent from each other. For example, either one of the first resonator 104 or the second resonator 106 may be employed for optical sensing, while the other resonator may be employed for tracing.

In the context of various embodiments, one or more electrical interconnections (e.g. wire or bus) may be connected to either the first resonator 104 or the second resonator 106, acting as the tracing resonator, for the application of a current (or a voltage). The first resonator and/or the second resonator may also include electrodes for the application of a current (or a voltage).

In the context of various embodiments, the term "resonator" may mean a component, a device or a system that exhibits resonance, where the device may oscillate or resonate at relatively larger amplitudes at particular frequencies, known as its resonant frequencies, compared to the amplitudes of the oscillations at non-resonant frequencies.

In the context of various embodiments, the cladding of the first resonator 104 may include or may be an oxide cladding, for example $SiO_2$ or InAlAs oxide ($InAlAs(O_x)$). The cladding may be formed using a CMOS-compatible fabrication process, for providing a cost effective optical sensing system.

In the context of various embodiments, the "effective refractive index" depends on the overall waveguide or resonator configuration, for example as a function of the refractive index of the core and the refractive index of the cladding of the waveguide or resonator.

Figure 2:
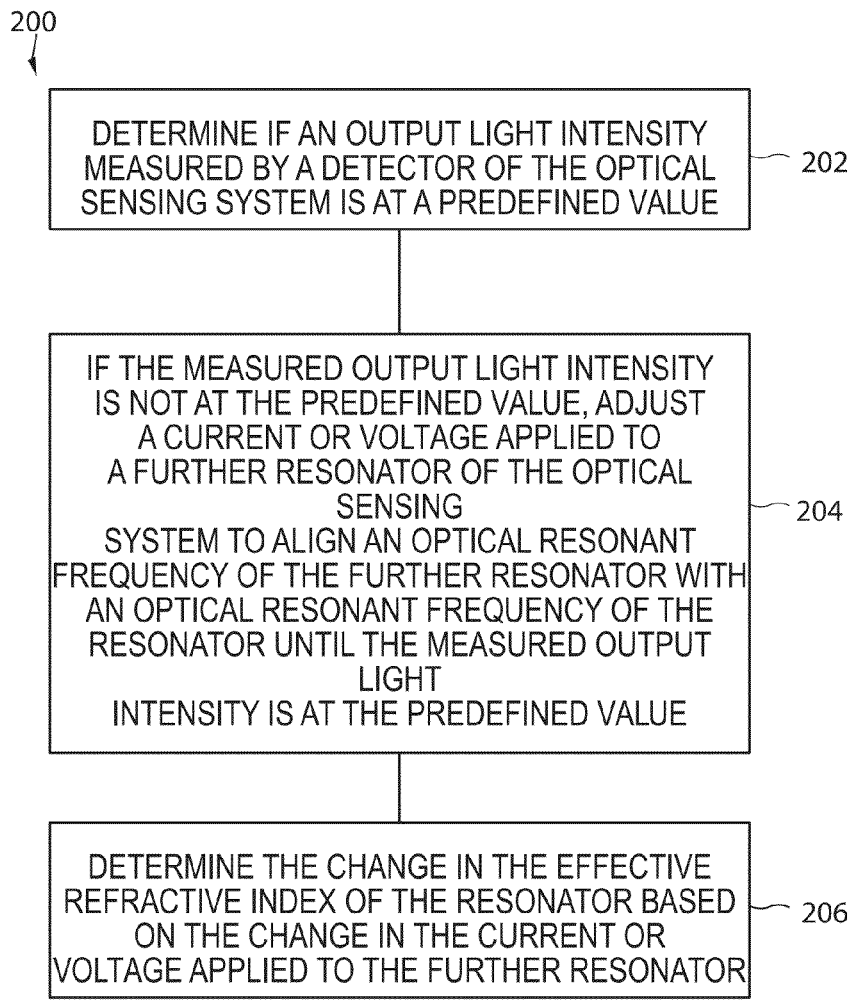
FIG. 2 shows a flow chart illustrating a method of determining a change in an effective refractive index of a resonator of an optical sensing system, according to various embodiments.

FIG. 2 shows a flow chart 200 illustrating a method of determining a change in an effective refractive index of a resonator of an optical sensing system, according to various embodiments.

At 202, it is determined if an output light intensity measured by a detector of the optical sensing system is at a predefined value. In other words, an output light intensity measured by a detector of the optical sensing system is determined as to whether the output light intensity is at a predefined value (e.g. a maximum value or intensity).

At 204, if the measured output light intensity is not at the predefined value, a current or voltage applied to a further resonator of the optical sensing system is adjusted to align an optical resonant frequency of the further resonator with an optical resonant frequency of the resonator until the measured output light intensity is at the predefined value.

At 206, the change in the effective refractive index of the resonator is determined based on the change in the current or voltage applied to the further resonator.

In various embodiments, the change in the effective refractive index of the resonator and the change in the current applied to the further resonator has a relationship of $$\Delta n_{\it eff} = 2ARI\Delta I \frac{n_g}{\lambda_0},$$

where $\Delta n_{\it eff}$ is the change in the effective refractive index of the resonator, A is thermal efficient (nm/W), R is the resistance of a thermal heater, I is the current applied to the further resonator, $\Delta I$ is the change in the current applied to the further resonator, $n_g$ is a group refractive index of the resonator, and $\lambda_0$ is the center wavelength of the resonator. In various embodiments, the further resonator includes the thermal heater.

In various embodiments, the method of determining a change in an effective refractive index of a resonator (e.g. a sensing resonator) of an optical sensing system may include receiving an optical signal (e.g. light) via an input optical waveguide, which then passes or couples a portion of the optical signal to the resonator (e.g. first resonator), coupling the optical signal from the resonator (e.g. optical signal that is dropped from the resonator) to a coupling optical waveguide, which then passes or couples a portion of the optical signal to a further resonator (e.g. second resonator), coupling the optical signal (e.g. optical signal that is dropped from the further resonator) from the further resonator (e.g. a tracing resonator) to an output optical waveguide, and receiving or detecting the optical signal from the output optical waveguide by a detector. A variable current (or a variable voltage) may be applied to the further resonator to tune a suitable parameter (e.g. optical resonant frequency) of the further resonator to achieve a predefined value (e.g. maximum intensity) of the output signal detected by the detector. The change in the current or voltage applied to the further resonator so as to achieve the predefined value of the detected optical signal may be determined in order to determine the corresponding change in the effective refractive index of the resonator (e.g. sensing resonator).

In the context of various embodiments, it should be appreciated that the first resonator (e.g. 104) and the second resonator (e.g. 106) are interchangeable. In other words, depending on the configuration of the optical sensing system (e.g. 100) or the resonator arrangement (e.g. 102), each of the first resonator (e.g. 104) and the second resonator (e.g. 106) may act as either a sensing resonator or a tracing resonator. The sensing resonator may be a passive element while the tracing resonator may be an active element, where a current or a voltage is applied.

In the context of various embodiments, the optical signal or light of interest that is detected by the detector, includes the light that is dropped from one resonator (e.g. the first resonator) which is then coupled to another resonator (e.g. the second resonator), and subsequently the light that is dropped by the other resonator (e.g. the second resonator). Therefore, the detector detects light that is dropped from two resonators.

In various embodiments, light may be coupled, for example from a waveguide, to a ring or microring resonator. Oscillation modes (with spatial wavelength) light may be coupled to the ring resonator and may propagate in the ring resonator, such that the oscillation modes may be lost, for example via a through port or a drop port. Some of the wavelength light, which does not satisfy the resonant condition (i.e. not resonant wavelength) may be passed 'through' by the ring resonator directly with a small loss and output from the through port. From the through port, oscillation modes show a valley-like shape in the spectrum. While the oscillation modes propagate in the ring resonator, in each propagation through a revolution of the ring resonator, a part of the light, which satisfies the resonant condition (i.e. light of the resonant wavelength) may be dropped from the ring resonator and output through the drop port. From the drop port, oscillation modes show a peak in the spectrum. In the drop port, only oscillation modes of resonant wavelength are present.

Various embodiments may provide a silicon microring resonator-based optical sensing system employing a dual-microring resonator structure, which may include two identically designed microring resonators. The dual-microring resonator optical sensing system employs the filter-cascading effect and enable the use of a broadband light source, thus significantly decreasing the cost.

Various embodiments of the optical sensing system, as compared to conventional devices employing wavelength-scanning method, may provide the following advantages: 1) the use of broadband light source inputs, rather than high-resolution wavelength tunable laser inputs, 2) voltage/current scanning with maximum intensity detection, instead of wavelength scanning, 3) sensing interrogation involving voltage/current change direct readout, rather than the detection of resonance wavelength shift, 4) narrowed resonance linewidth as a result of the filter-cascading effect, thus enhancing the sensing sensitivity, and 5) the detection limit is determined by the resolution of the voltage/current supply source, rather than the tunable laser resolution. In addition, the use of a broadband light source rather than a high-resolution wavelength-tunable laser reduces the cost. Furthermore, the optical sensing system of various embodiments has a compact footprint and may be integrated (e.g. planar integration) with CMOS-compatible fabrication process.

The optical sensing system of various embodiments may be used in various application including medical diagnosis, healthcare and environmental monitoring, amongst others.

Figure 3A:
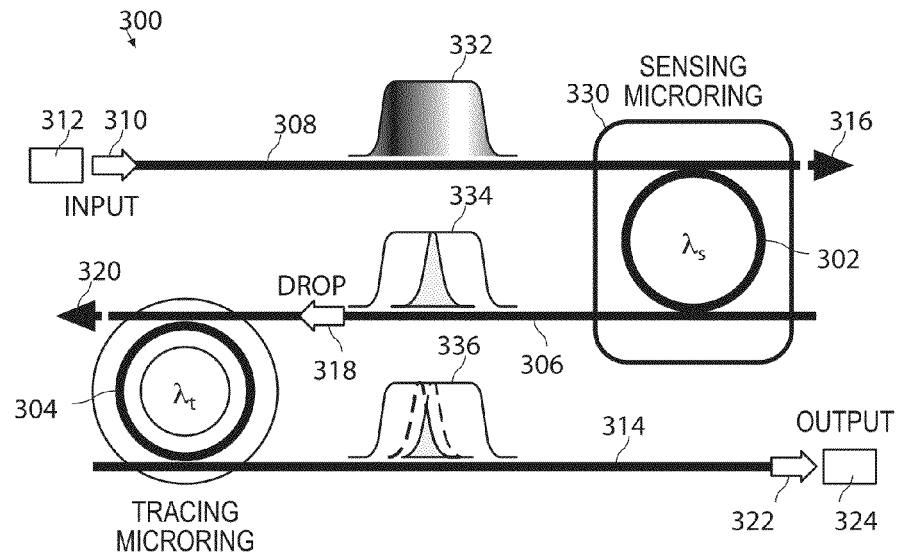
FIG. 3A shows a schematic view of an optical sensing system, according to various embodiments.

FIG. 3A shows a schematic view of an optical sensing system 300, according to various embodiments. The optical sensing system 300 is a microring-resonator-based optical sensing system, having two microring resonators separately for optical sensing and tracing. In various embodiments, the two microring resonators may be identically designed.

The optical sensing system 300 includes a resonator arrangement including a sensing microring (sensing resonator) 302 and a tracing microring (tracing resonator) 304. An effective refractive index of the sensing resonator 302 may be changeable in response to a change in a refractive index of a cladding (e.g. upper cladding layer) of the sensing resonator 302. A current or a voltage being adjustable in response to a change in the effective refractive index of the sensing resonator 302 may be applied to the tracing resonator 304, wherein the optical sensing system 300 may be configured to determine the change in the effective refractive index of the sensing resonator 302 based on a change in the current or voltage applied to the tracing resonator 304. The sensing resonator 302 may have a resonant wavelength, $\lambda_s$, while the tracing resonator 304 may have a resonant wavelength, $\lambda_t$. Where the sensing resonator 302 and the tracing resonator 304 are identical, $\lambda_s$ is at least substantially equal to $\lambda_t$, at the original or initial state of the optical sensing system 300.

The optical sensing system 300 further includes a coupling optical waveguide 306 coupled between the sensing resonator 302 and the tracing resonator 304, where the coupling optical waveguide 306 is configured to guide light received from the sensing resonator 302 to the tracing resonator 304.

The optical sensing system 300 may further include an input optical waveguide 308 configured to guide received light (e.g. an input light), for example an optical signal or light, as represented by the arrow 310, for example from a wideband or broadband source 312. The input light 310 may be broadband, having a spectrum 332 covering a range of wavelengths. As shown in FIG. 3A, the sensing resonator 302 is coupled to the input optical waveguide 308 to receive the light 310 from the input optical waveguide 308.

The optical sensing system 300 may further include an output optical waveguide 314 coupled to the tracing resonator 304, the output optical waveguide 314 being configured to output light received from the resonator arrangement or the tracing resonator 304.

As illustrated in FIG. 3A, a portion of the input light 310 may pass through the sensing resonator 302, as represented by the arrow 316, and is outputted to a through port, and a portion of the input light 310 may be coupled to the sensing resonator 302, which may propagate and cycle through and within the sensing resonator 302, where part of the light, as represented by the arrow 318, may be dropped and coupled to the coupling optical waveguide 306. The light 318 may have a spectrum 334 having a peak wavelength corresponding at least substantially to $\lambda_s$. Therefore, the sensing resonator 302 may function as a microring filter. During sensing operation where the effective refractive index of the sensing resonator 302 is changed, the optical resonance of the sensing resonator 302 is changed, thereby changing or shifting the resonant wavelength $\lambda_s$ to $\lambda_{s'}$.

A portion of the light 318 may pass through the tracing resonator 304, as represented by the arrow 320, and is outputted to a through port, and a portion of the light 318 may be coupled to the tracing resonator 304, which may propagate and cycle through and within the tracing resonator 304, where part of the light, as represented by the arrow 322, may be dropped and coupled to the output optical waveguide 314. The light 322 may then be outputted to a detector 324 coupled to the output optical waveguide 314 to measure an intensity of the light 322 received from the output optical waveguide 314.

The light 322 may have a spectrum 336 with a reduced intensity, resulting from the misalignment of the respective optical resonances of the sensing resonator 302 and the tracing resonator 304. For example, during sensing operation, the resonant wavelength of the sensing resonator may have been shifted to $\lambda_{s'}$, which is not aligned with $\lambda_t$, thereby resulting in spectrum 336 with a reduced intensity. In order to increase or maximise the intensity, the optical resonance of the tracing resonator 304 may be tuned via electro-optic or thermo-optic effect to shift the resonant wavelength $\lambda_t$ to $\lambda_{t'}$ such that $\lambda_{t'}$ is at least substantially equal to $\lambda_{s'}$, as a result of a change in the refractive index or effective refractive index of the tracing resonator 304.

The square box 330 illustratively show the sensing window of the optical sensing system 300, for sensing stimuli or constituents of a sample, for example a biological sample and/or a chemical sample.

Each of the input optical waveguide 308, the coupling optical waveguide 306 and the output optical waveguide 314 may be an at least substantially straight waveguide. However, it should be appreciated that each of the input optical waveguide 308, the coupling optical waveguide 306 and the output optical waveguide 314 may have other configurations, for example a bend waveguide. Furthermore, each of the input optical waveguide 308, the coupling optical waveguide 306 and the output optical waveguide 314 may have different configurations.

In various embodiments, the sensing resonator 302 acts as a sensing element to sense a change in the effective refractive index of the sensing resonator 302, which may result in a shift in the resonance wavelength of the sensing resonator 302. The tracing resonator 304 acts as a tracing element to trace the resonance wavelength shift of the sensing resonator 302 due to the refractive index change, by either thermo-optic (TO) or electro-optic (EO) effect. The drop-port transmission (e.g. 318) from the sensing resonator 302 feeds to the tracing resonator 304, and the drop-port output (e.g. 322) from the tracing resonator 304 is monitored. In embodiments where the tracing resonator 304 traces the resonance wavelength shift of the sensing resonator 302 by thermo-optic (TO) effect, the tracing resonator 304 includes a thermal heater. A current or voltage is applied to the tracing resonator 304 (e.g. to the thermal heater) to increase the temperature of the tracing resonator 304 so as to tune the optical resonance of the tracing resonator 304.

While FIG. 3A shows that the sensing resonator 302 is coupled to the input optical waveguide 308 and the coupling optical waveguide 306, and that the tracing resonator 304 is coupled to the coupling optical waveguide 306 and the output optical waveguide 314, it should be appreciated that the positions of the sensing resonator 302 and the tracing resonator 304 may be interchangeable such that the sensing resonator 302 is coupled to the coupling optical waveguide 306 and the output optical waveguide 314 and the tracing resonator 304 is coupled to the input optical waveguide 308 and the coupling optical waveguide 306.

Figure 3B:
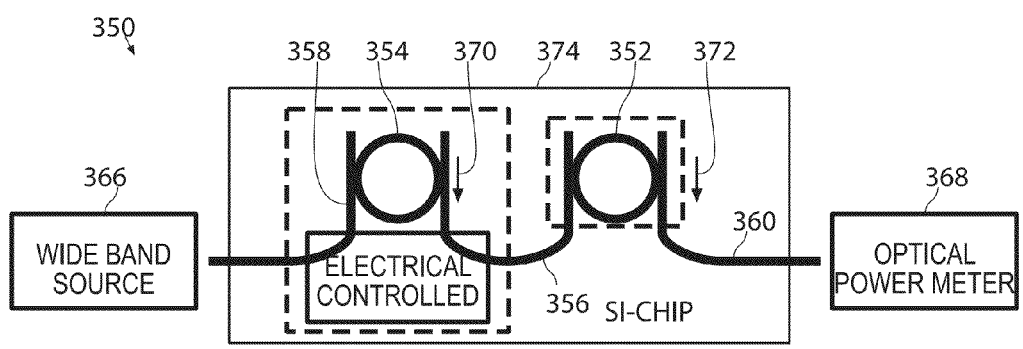
FIG. 3B shows a schematic view of an optical sensing system, according to various embodiments.

FIG. 3B shows a schematic view of an optical sensing system 350, according to various embodiments. The optical sensing system 300 includes a resonator arrangement including a sensing resonator 352 and a tracing resonator 354. The optical sensing system 350 further includes a coupling optical waveguide 356 coupled between the sensing resonator 352 and the tracing resonator 354, where the coupling optical waveguide 356 is configured to guide light received from the tracing resonator 354 to the sensing resonator 352.

The optical sensing system 350 may further include an input optical waveguide 358 configured to guide an input optical signal or light, for example from a wideband or broadband source 366. The input optical waveguide 358 is coupled to the tracing resonator 354. The optical sensing system 350 may further include an output optical waveguide 360 coupled to the sensing resonator 352, the output optical waveguide 360 being configured to output light received from the resonator arrangement or the sensing resonator 352 to a detector, for example an optical power meter 368.

The sensing resonator 352, the tracing resonator 354, the input optical waveguide 358, the coupling optical waveguide 356 and the output optical waveguide 360 may be formed or fabricated on a substrate, for example a silicon chip (Si-chip) 374.

Features, elements or components of the optical sensing system 350 that are similarly present in the optical sensing system 300 (FIG. 3A) may be as described in the context of the optical sensing system 300.

Each of the input optical waveguide 358, the coupling optical waveguide 356 and the output optical waveguide 360 may be a bend waveguide. However, it should be appreciated that each of the input optical waveguide 358, the coupling optical waveguide 356 and the output optical waveguide 360 may have other configurations, for example a straight waveguide. Furthermore, each of the input optical waveguide 358, the coupling optical waveguide 356 and the output optical waveguide 360 may have different configurations.

In various embodiments, the sensing resonator 352 acts as a sensing element to sense a change in the effective refractive index of the sensing resonator 352, for example in response to a stimulus, which may result in a shift in the resonance wavelength of the sensing resonator 352. The tracing resonator 354 acts as a tracing element to trace the resonance wavelength shift of the sensing resonator 352 due to the refractive index change, by either thermo-optic (TO) or electro-optic (EO) effect. The drop-port transmission, as represented by the arrow 370, from the tracing resonator 354 feeds to the sensing resonator 352, and the drop-port output, as represented by the arrow 372, from the sensing resonator 352 is monitored by the optical power meter 368. In embodiments where the tracing resonator 354 traces the resonance wavelength shift of the sensing resonator 352 by thermo-optic (TO) effect, the tracing resonator 354 includes a thermal heater. A current or voltage is applied to the tracing resonator 354 (e.g. to the thermal heater) to increase the temperature of the tracing resonator 354 so as to tune the optical resonance of the tracing resonator 354.

While FIG. 3B shows that the tracing resonator 354 is coupled to the input optical waveguide 358 and the coupling optical waveguide 356, and that the sensing resonator 352 is coupled to the coupling optical waveguide 356 and the output optical waveguide 360, it should be appreciated that the positions of the sensing resonator 352 and the tracing resonator 354 may be interchangeable such that the tracing resonator 354 is coupled to the coupling optical waveguide 356 and the output optical waveguide 360 and the sensing resonator 352 is coupled to the input optical waveguide 358 and the coupling optical waveguide 356.

Figure 3C:
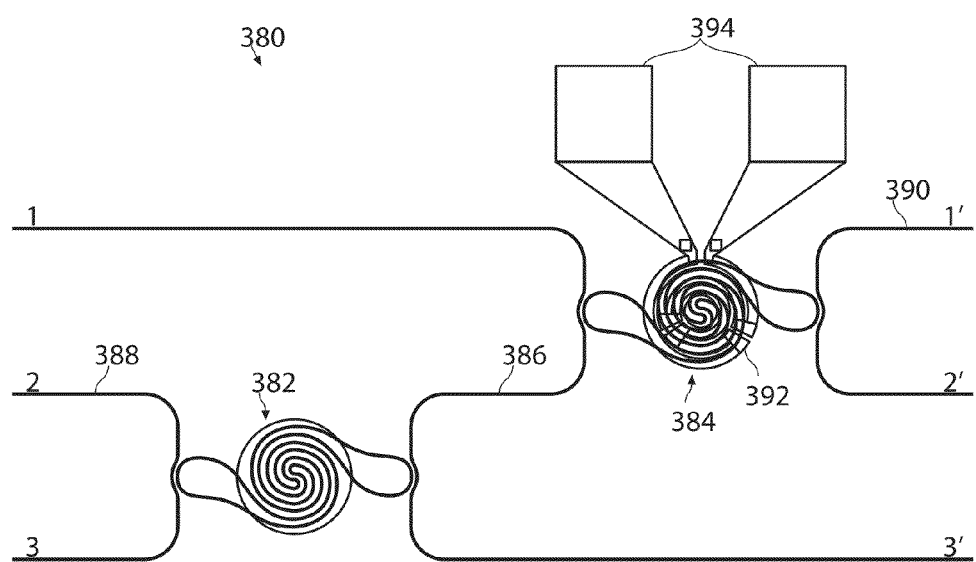
FIG. 3C shows a schematic view of an optical sensing system, according to various embodiments.

FIG. 3C shows a schematic view of an optical sensing system 380, according to various embodiments. The optical sensing system 380 includes a resonator arrangement including a sensing resonator 382 and a tracing resonator 384. The optical sensing system 380 further includes a coupling optical waveguide 386 coupled between the sensing resonator 382 and the tracing resonator 384, where the coupling optical waveguide 386 is configured to guide light received from the sensing resonator 382 to the tracing resonator 384.

The optical sensing system 380 may further include an input optical waveguide 388 configured to guide an input optical signal or light, for example from a wideband or broadband source (not shown). The input optical waveguide 388 is coupled to the sensing resonator 382. The optical sensing system 380 may further include an output optical waveguide 390 coupled to the tracing resonator 384, the output optical waveguide 390 being configured to output light received from the resonator arrangement or the tracing resonator 384 to a detector (not shown).

The optical sensing system 380 or the tracing resonator 384 may further include a heater or a thermal heater (e.g. a microheater) 392 including a pair of electrodes 394 formed or arranged in proximity to the tracing resonator 384, for example over the tracing resonator 384. The thermal heater 392 may be employed to supply heat to the tracing resonator 384 to change the refractive index or effective refractive index of the tracing resonator 384 for tracing the effective refractive index change of the sensing resonator 382, as a result of TO effect. However, it should be appreciated that in embodiments of optical sensing system 380 employing the EO effect, the thermal heater 392 may not be in operation or the tracing resonator 384 may not include the thermal heater 392.

Features, elements or components of the optical sensing system 380 that are similarly present in the optical sensing system 300 (FIG. 3A) and/or optical sensing system 350

(FIG. 3B) may be as described in the context of the optical sensing system 300 and/or optical sensing system 350.

Each of the input optical waveguide 388, the coupling optical waveguide 386 and the output optical waveguide 390 may be a bend waveguide. However, it should be appreciated that each of the input optical waveguide 388, the coupling optical waveguide 386 and the output optical waveguide 390 may have other configurations, for example a straight waveguide. Furthermore, each of the input optical waveguide 388, the coupling optical waveguide 386 and the output optical waveguide 390 may have different configurations.

In various embodiments, the sensing resonator 382 acts as a sensing element to sense a change in the effective refractive index of the sensing resonator 382, for example in response to a stimulus, which may result in a shift in the resonance wavelength of the sensing resonator 382. The tracing resonator 384 acts as a tracing element to trace the resonance wavelength shift of the sensing resonator 382 due to the refractive index change, by either thermo-optic (TO) or electro-optic (EO) effect.

In various embodiments, an optical signal or light may be provided to port 1 of the coupling optical waveguide 386 and the light from port 1' of the output optical waveguide 390 may be monitored to determine the 'drop' status of the tracing resonator 384. A portion of the light from port 1 is coupled via the coupling optical waveguide 386 to the tracing resonator 384, where a portion of the light coupled into the tracing resonator 384 is dropped via the output optical waveguide 390 to port 1'.

In various embodiments, an optical signal or light may be provided to port 3 of the input optical waveguide 388 and the light from port 3' of the coupling optical waveguide 386 may be monitored to determine the 'drop' status of the sensing resonator 382. A portion of the light from port 3 is coupled via the input optical waveguide 388 to the sensing resonator 382, where a portion of the light coupled into the sensing resonator 382 is dropped via the coupling optical waveguide 386 to port 3'.

In various embodiments, an optical signal or light may be provided to port 1 of the coupling optical waveguide 386 and the light from port 3' of the coupling optical waveguide 386 may be monitored to determine the 'through' status of the tracing resonator 384 and the sensing resonator 382. A portion of the light from port 1 passes through the tracing resonator 384 and the sensing resonator 382 via the coupling optical waveguide 386 to port 3'.

In various embodiments, an optical signal or light may be provided to port 3 of the input optical waveguide 388 and the light from port 1' of the output optical waveguide 390 may be monitored to determine the 'through' status of the sensing resonator 382 and the tracing resonator 384. A portion of the light from port 3 passes through the sensing resonator 382 via the coupling optical waveguide 386 to the tracing resonator 384, where a portion of the light coupled into the tracing resonator 384 passes through via the output optical waveguide 390 to port 1'.

In various embodiments, an optical signal or light may be provided to port 2 of the input optical waveguide 388 and the light from port 2' of the output optical waveguide 390 may be monitored for sensing a target or a sample. A portion of the light from port 2 is dropped from the sensing resonator 382 and couples via the coupling optical waveguide 386 to the tracing resonator 384, where a portion of the light coupled into the tracing resonator 384 is dropped via the output optical waveguide 390 to port 2'. A detector may be provided at port 2' to detect the optical signal or light received, after target sensing.

While FIG. 3C shows that the sensing resonator 382 is coupled to the input optical waveguide 388 and the coupling optical waveguide 386, and that the tracing resonator 384 is coupled to the coupling optical waveguide 386 and the output optical waveguide 390, it should be appreciated that the positions of the sensing resonator 382 and the tracing resonator 384 may be interchangeable such that the sensing resonator 382 is coupled to the coupling optical waveguide 386 and the output optical waveguide 390 and the tracing resonator 384 is coupled to the input optical waveguide 388 and the coupling optical waveguide 386.

Figure 4:
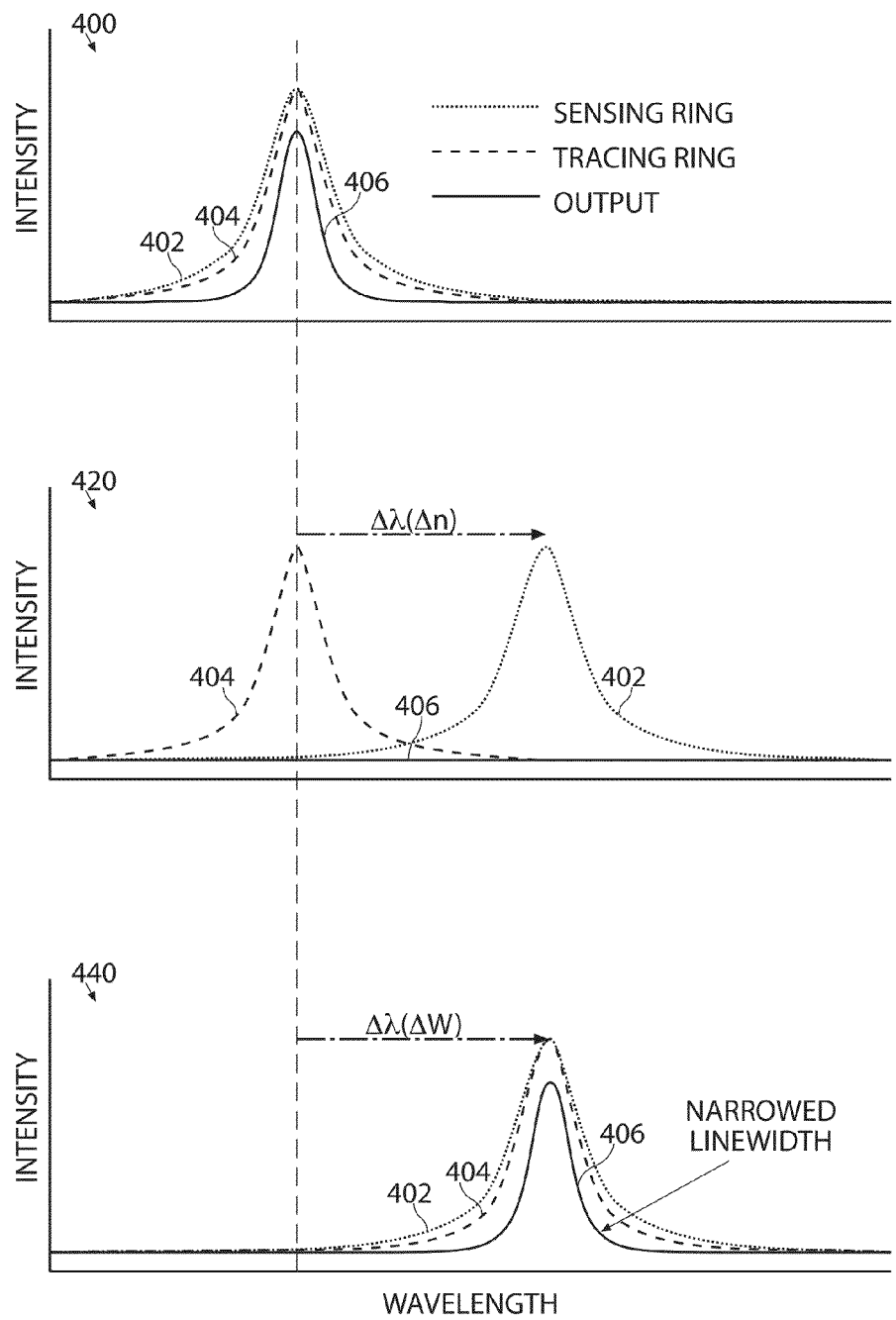
FIG. 4 shows plots of optical resonances of the optical sensing system of various embodiments, illustrating the working principle of the optical sensing system.

FIG. 4 shows plots 400, 420, 440, of optical resonances of the optical sensing system of various embodiments, illustrating the working principle of the optical sensing system, based on the filter-cascading effect. As a result of the filter-cascading effect for a dual microring-cascaded system, the maximum output intensity occurs when the respective resonances of the two microrings (e.g. the sensing resonator and the tracing resonator) are aligned. In other words, the maximum output intensity occurs when the two microring resonators have at least substantially similar resonant wavelength or resonant frequency.

In various embodiments, the two microring resonators may be identical. In the original or initial state, the optical resonances for the two identically designed microring resonators may be at least substantially aligned with each other. As shown in the plot 400, the optical resonance 402 of the sensing resonator (sensing ring) and the optical resonance 404 of the tracing resonator (tracing ring) are aligned with each other, at an at least substantially similar resonant wavelength. Therefore, the intensity of the output 406 from the optical sensing system may be at a maximum.

When the sensing resonator is employed for sensing, the refractive index of the cladding of the sensing resonator may change as a response to a stimulus, thereby changing the effective refractive index of the sensing resonator. As shown in the plot 420, after sensing, the resonance 402 of the sensing resonator may be red-shifted (i.e. the resonant wavelength is shifted to a longer wavelength), while the resonance 404 of the tracing resonator may remain at the original state, thus resulting in a decrease in the intensity of the output 406 of the optical sensing system. Therefore, the resonant wavelength change, $\Delta\lambda$, of the sensing resonator is due to an effective refractive index change of the sensing resonator, as a result of a refractive index change of the cladding of the sensing resonator. In plot 420, $\Delta n$ refers to the change in the effective refractive index change of the sensing resonator.

Subsequently, electro-optic (EO) effect or thermo-optic (TO) effect may be employed to red-shift the resonance of the tracing resonator in order to increase the output intensity of the optical sensing system, for example to the maximum intensity. As shown in the plot 440, for example after TO tuning, the resonance 404 of the tracing resonator may be red-shifted to at least substantially align with the resonance 402 of the sensing resonator, thus resulting in an increase in the intensity of the output 406 of the optical sensing system, for example to maximum intensity. In addition, the filter-cascading effect narrows the resonance linewidth of the output 406, thereby enhancing the sensing sensitivity.

Examples and results as described hereinafter is based on thermo-optic (TO) effect, as an example and for illustrative purposes. However it should be appreciated that both EO and TO tunings or effects may be realized by supplying a current or voltage to the tracing resonator, although using different mechanisms. Using EO tuning, the current or voltage is applied to the tracing resonator (e.g. p-n/p-i-n diode) to generate free carriers, thus changing the refractive index or effective refractive index of the tracing resonator so as to change the optical resonance of the tracing resonator. Using TO tuning, the current or voltage is applied to the tracing resonator, e.g. to a thermal heater of the tracing resonator to generate heat, thus changing the temperature of the tracing resonator, thereby changing the refractive index or effective refractive index of the tracing resonator so as to change the optical resonance of the tracing resonator. Therefore, the results obtained using the EO effect or the TO effect may be at least substantially similar. However, there may be a difference in terms of the resonance shift, for example the amount of resonance shift.

As an example for employing TO tuning, variable power may be applied to the tracing resonator (i.e. to the thermal heater of the tracing resonator) to tune the optical resonance of the tracing resonator. Therefore, the resonant wavelength change, $\Delta\lambda$, of the tracing resonator may be due to a power change, $\Delta W$, applied to the tracing resonator, for effecting thermo-optic tuning of the tracing resonator. Hence, by reading or determining the power supplied to the tracing resonator (e.g. to the thermal heater), the effective refractive index change of the sensing resonator may be determined.

In various embodiments, A) may be proportional to $\Delta n$ (i.e. $\Delta\lambda \propto \Delta n$) and $\Delta\lambda$ may be proportional to $\Delta W$ (i.e. $\Delta\lambda \propto \Delta W$). Therefore, $\Delta n$ may be proportional to $\Delta W$ (i.e. $\Delta n \propto \Delta W$).

Figure 5:
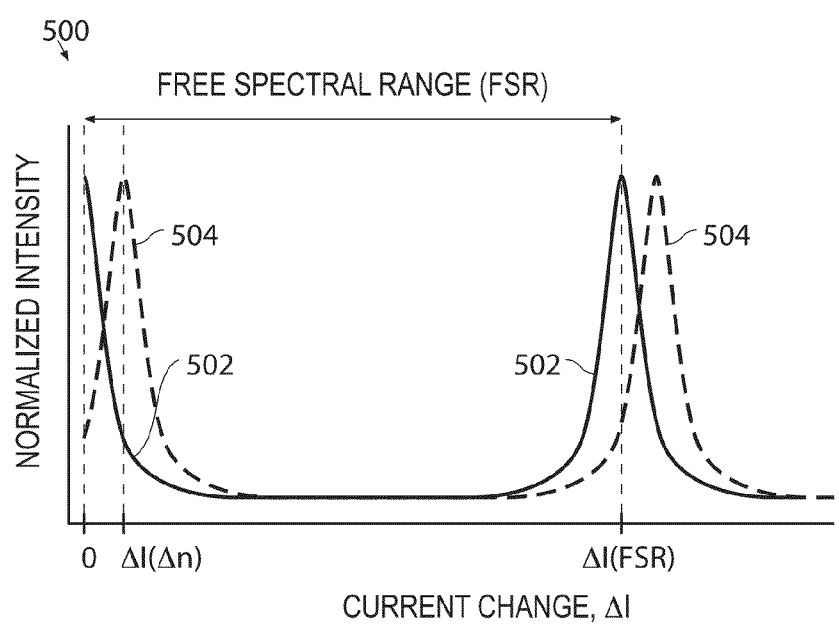
FIG. 5 shows a plot of the transmission spectra as a function of current change of an optical sensing system, according to various embodiments.

In various embodiments, the change in the power, $\Delta W$, supplied to the tracing resonator may be determined by scanning the voltage or current supplied so as to determine the transmission spectrum or output spectrum of the optical sensing system according to the change in the voltage or current. FIG. 5 shows a plot 500 of the transmission spectra as a function of current change of an optical sensing system, according to various embodiments, illustrating the transmission spectrum 502 before optical sensing and the transmission spectrum 504 after optical sensing. The plot 500 may be obtained by numerical analysis.

As illustrated in the plot 500, the refractive index change $\Delta n$, for example the change in the effective refractive index change of the sensing resonator, may be determined by reading out or determining the current change $\Delta I(\Delta n)$ from the spectrum 504. In addition, the free spectral range of the spectrum 502 may be determined by reading out or determining the current change $\Delta I$(FSR) from the spectrum 502. The term "free spectral range (FSR)" as used herein may refer to the spacing in optical frequency or wavelength between two successive reflected or transmitted optical intensity maxima or minima. In other words, the periodic peaks have a period as determined from $\Delta I$(FSR).

The wavelength change due to the electrical power supply induced thermo-optical effect may be approximately expressed as:

$$\lambda = AW + C = ARI^2 + C = \frac{AV^2}{R} + C \quad \text{(Equation 1)}$$

where A is thermal efficient with a unit of nm/W, W is power, R is resistance, for example, of a thermal heater, I is current applied to the tracing resonator and C is a constant value. Power, W, may be expressed as VI or $RI^2$ or $V^2/R$, where V is voltage and has the relationship V=RI.

Based on equation 1, the relationship between the resonance wavelength shift, $\Delta\lambda$, and the current change, $\Delta I$, may be given by the equation:

$$\Delta\lambda = 2ARI\Delta I = \frac{2AV\Delta V}{R}. \quad \text{(Equation 2)}$$

In a microring resonator, the relationship between the resonance shift, $\Delta\lambda$, and the effective refractive index change, $\Delta n_{eff}$, may be given by the equation:

$$\Delta\lambda = \frac{\lambda_0}{n_g}\Delta n_{eff} \quad \text{(Equation 3)}$$

where $n_g$ is the group index of the sensing resonator, $\lambda_0$ is the center wavelength of the sensing resonator and $n_{eff}$ is the effective refractive index of the sensing resonator.

Therefore, based on equations 2 and 3, the relationship between the effective refractive index change, $\Delta n_{eff}$, and the current change, $\Delta I$, may be given by the equation:

$$\Delta n_{eff} = 2ARI\Delta I \frac{n_g}{\lambda_0}. \quad \text{(Equation 4)}$$

In various embodiments, the use of the voltage/current scanning method enables the adoption or use of broadband light sources to provide an input light, which eliminates the use of high-resolution wavelength-scanning lasers. Therefore, the detection limit of the optical sensing system of various embodiments depends on the voltage/current sensitivity, where it is much easier to achieve a high resolution current source, compared to the challenge in obtaining a high resolution wavelength-tunable laser, which is a barrier towards achieving small or low detection limit.

The detection limit, DL (RIU), may be defined by the equation:

$$DL = \Delta\lambda/S \quad \text{(Equation 5)}$$

where S is the sensitivity.

Using a channel waveguide as an example and not limitations, the sensing sensitivity S may be calculated numerically for the channel waveguide. FIG. 6 shows results of numerical simulations for calculating the sensing sensitivity for a channel waveguide structure on silicon-on-insulator (SOI).

Figure 6A:
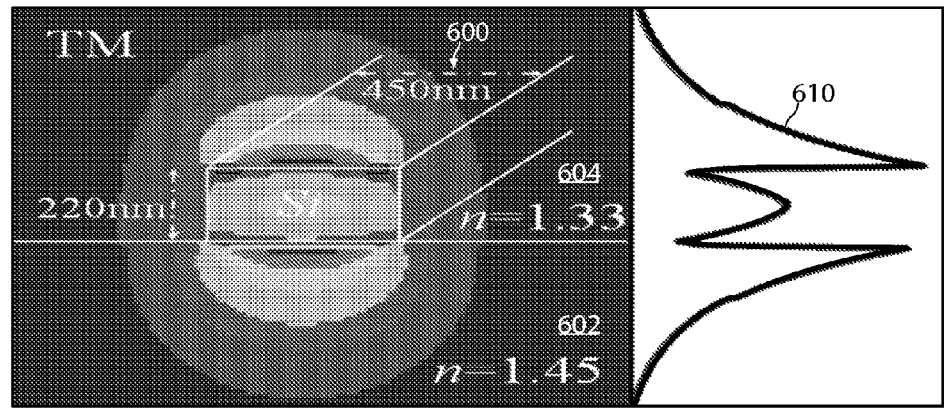
FIGS. 6A through 6C show results of numerical simulations for calculating the sensing sensitivity for a channel waveguide structure on silicon-on-insulator (SOI).

FIG. 6A shows a silicon (Si) channel waveguide 600 having a thickness of about 220 nm and a width of about 450 nm, on a SOI 602, with the simulated mode field pattern for a transverse magnetic (TM) mode and the corresponding intensity profile 610 of the TM mode. The SOI includes a silicon oxide (SiO) layer having a refractive index of about 1.45. The Si channel waveguide 600, having a refractive index of about 3.45, is surrounded by a cladding 604 having a refractive index of about 1.33. The mode field extends outside of the channel waveguide 600 and interacts or couples with the cladding layer 604, thereby enabling sensing of a change in the refractive index of the cladding 604.

Figure 6B:
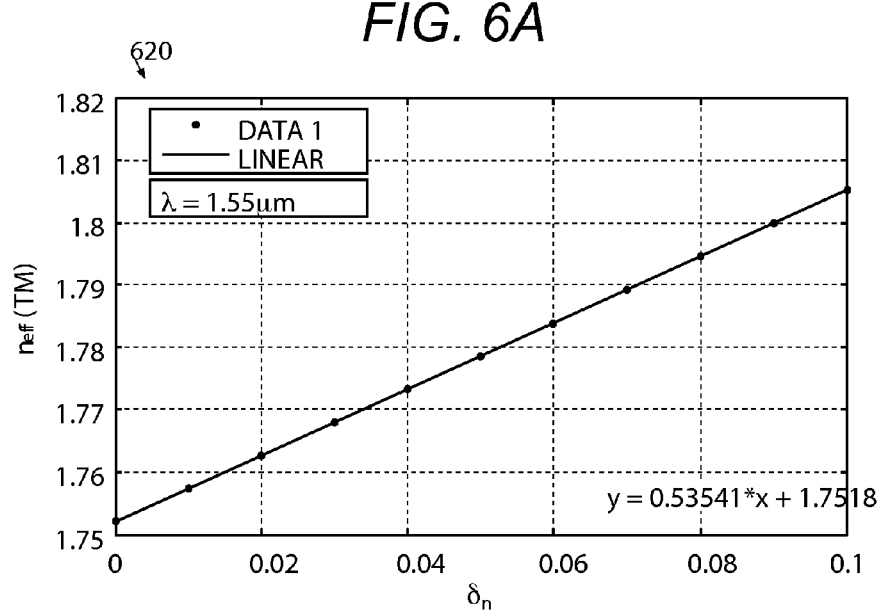
Figure 6C:
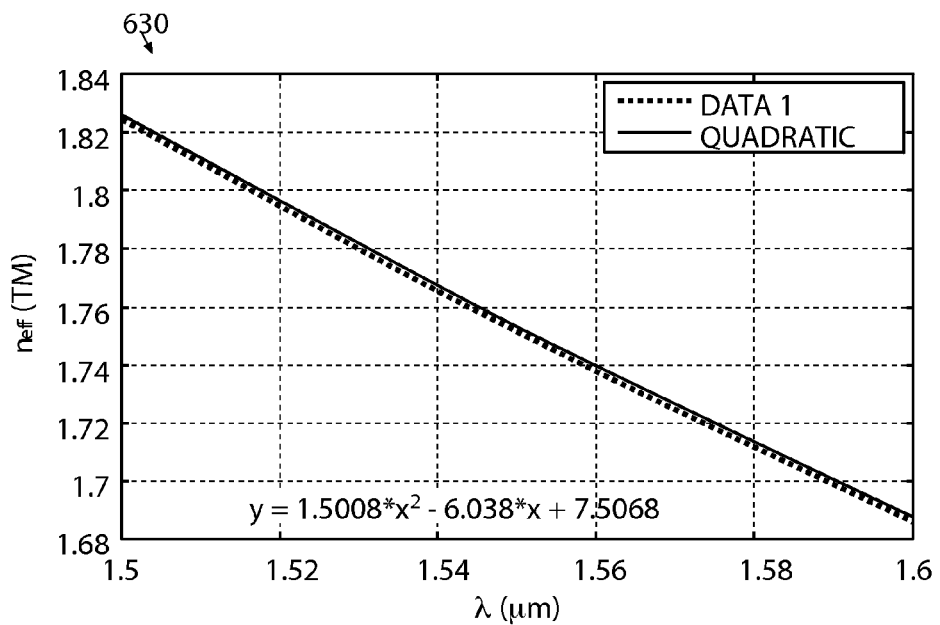

FIGS. 6B and 6C show plots 620, 630, illustrating the calculated effective refractive index change, based on the TM mode, as functions of the refractive index change, $\delta n$, of the upper cladding layer 604 and the wavelength, $\lambda$, respectively. The fitting parameters are shown in the plots 620, 630, where the calculated data of the plot 620 may be fitted with a linear fit having the relationship (y=0.53541x+1.7518), while the calculated data of the plot 630 may be fitted with a quadratic fit having the relationship (y=1.5008x²−6.038x+7.5068).

Therefore, from the results of plots 620, 630 of FIGS. 6B and 6C, the sensing sensitivity may be calculated based on the equation:

$$S = \frac{\partial \lambda}{\partial n_{clad}} \qquad \text{(Equation 6)}$$

$$= \frac{\lambda_0}{n_g} \frac{\partial n_{eff}}{\partial n_{clad}}$$

$$= \frac{\lambda_0}{n_{eff} - \lambda_0 \left( \frac{\partial n_{eff}}{\partial \lambda} \right)} \frac{\partial n_{eff}}{\partial n_{clad}},$$

resulting in a sensitivity of approximately 212.73 nm/RIU, where $\lambda_0$=1550 nm, $n_g$~3.9, $\partial n_{eff}/\partial n_{clad}$~0.53541 and $n_{eff}$~7.5068.

Based on equation 2 and J. Song, et al., *Opt. Express* 16, pp. 15304-15311 (2008), the entire disclosure of which is incorporated herein by reference, the resonance wavelength change, $\Delta\lambda$, as a function of the current change, $\Delta I$, may be calculated or approximated using the equation:

$$\Delta\lambda(\text{nm}) = 80\Delta I(\text{Ampere}) \qquad \text{(Equation 7)}$$

with RI approximately 0.5 V assuming R=50Ω and A approximately 0.08 nm/mW.

Therefore, the detection limit, DL (RIU), may be calculated, based on equations 5, 6 and 7, to be approximately $5.6 \times 10^{-6}$ RIU, assuming 15 μA current sensitivities (i.e. $\Delta I$=15 μA; $\Delta\lambda$(nm)=$1.2 \times 10^{-3}$). This is comparable to the wavelength-scanning method which may have a demonstrated best detection limit of approximately $10^{-7}$, but with a significantly lower cost. Furthermore, assuming 100 pA current sensitivities (i.e. $\Delta I$=100 pA; $\Delta\lambda$ (nm)=$8.0 \times 10^{-9}$), the detection limit is approximately $3.8 \times 10^{-11}$ RIU. In various embodiments, the detection limit may be between about $10^{-5}$ RIU and about $10^{-11}$ RIU, depending on the power supply (or current/voltage supply).

Figure 7A:
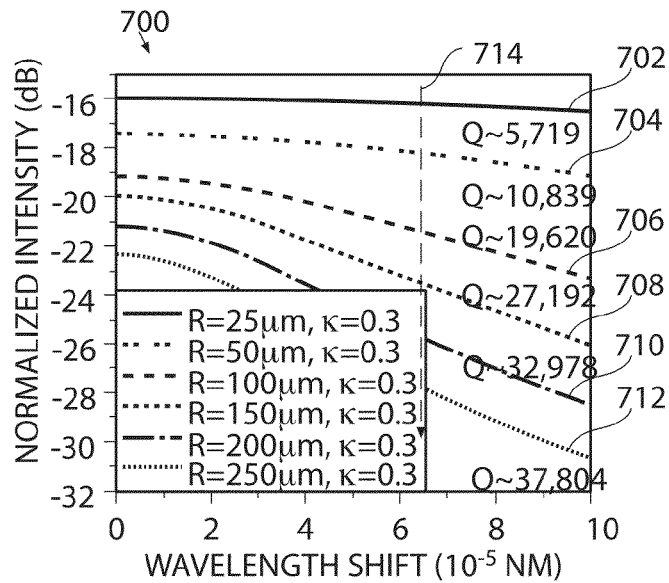
FIG. 7A shows a plot of normalized intensity as a function of wavelength shift for different radii of a microring resonator, according to various embodiments.

FIG. 7A shows a plot 700 of normalized intensity as a function of wavelength shift for different radii of a microring resonator, according to various embodiments. The plot 700 may be obtained by numerical analysis, for a constant coupling coefficient, κ, of 0.3, $n_{eff}$ of 1.8 for a TM mode and a propagation loss of 3 dB/cm. The coupling coefficient relates to the waveguide-microring resonator coupling.

The plot 700 shows the results for a microring resonator with different radii, R=25 μm 702, R=50 μm 704, R=100 μm 706, R=150 μm 708, R=200 μm 710 and R=250 μm 712. The arrow, as represented by 714, shows the direction of increasing radius of the microring resonator. The plot 700 also shows that as the radius of the microring resonator increases, the quality factor, Q, also increases, and as the quality factor, Q, increases, the difference in the output intensity for the microring resonator with different radii increases.

Figure 7B:
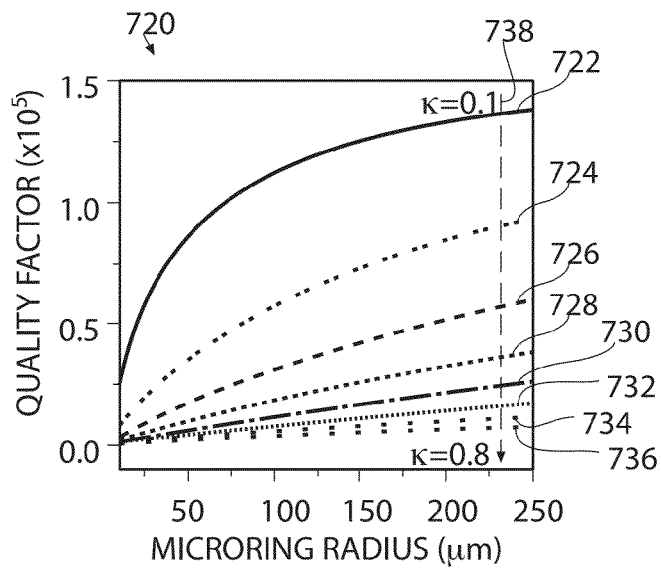
FIG. 7B shows a plot of quality factor as a function of microring radius for different coupling coefficients, according to various embodiments.

FIG. 7B shows a plot 720 of quality factor as a function of microring radius for different coupling coefficients, according to various embodiments. The plot 720 may be obtained by numerical analysis, for $n_{eff}$ of 1.8 for a TM mode and a propagation loss of 3 dB/cm. The plot 720 shows the results for a microring resonator with different coupling coefficients, κ=0.1 722, κ=0.2 724, κ=0.3 726, κ=0.4 728, κ=0.5 730, κ=0.6 732, κ=0.7 734 and κ=0.8 736. The arrow, as represented by 738 shows the direction of increasing coupling coefficient, κ, for the microring resonator.

Figure 7C:
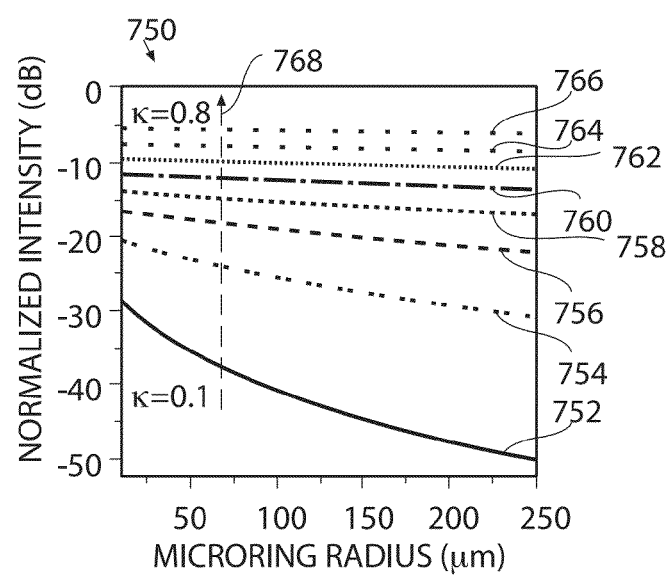
FIG. 7C shows a plot of normalized intensity as a function of microring radius for different coupling coefficients, according to various embodiments.

FIG. 7C shows a plot 750 of normalized intensity as a function of microring radius for different coupling coefficients, according to various embodiments. The plot 750 may be obtained by numerical analysis, for $n_{eff}$ of 1.8 for a TM mode and a propagation loss of 3 dB/cm. The plot 750 shows the results for microring resonators with different coupling coefficients, κ=0.1 752, κ=0.2 754, κ=0.3 756, κ=0.4 758, κ=0.5 760, κ=0.6 762, κ=0.7 764 and κ=0.8 766. The arrow, as represented by 768 shows the direction of increasing coupling coefficient, κ, for the microring resonator.

The results of FIGS. 7A to 7C show that as the radius, R, of a microring resonator increases, the quality factor, Q, increases while the output intensity decreases. In addition, as the coupling coefficient, κ, increases, the quality factor, Q, decreases while the output intensity increases. Therefore, there is a trade-off in the design in terms of the radius and the coupling coefficient of a ring or microring resonator in order to achieve a balance between the quality factor, Q, and the output intensity.

In various embodiments, the sensing sensitivity may be enhanced by enhancing the microring resonator quality factor, for example by balanced microring radius and waveguide-microring coupling. The insertion loss may also be minimised for power detection via enhancement in the design and fabrication process. In addition, on-chip detector or photodetector and/or on-chip light source may be integrated with the optical sensing system of various embodiments. Feedback systems may also be added.

While the invention has been particularly shown and described with reference to specific embodiments, it should be understood by those skilled in the art that various changes in form and detail may be made therein without departing from the spirit and scope of the invention as defined by the appended claims. The elements of the various embodiments may be incorporated into each of the other species to obtain the benefits of those elements in combination with such other species, and the various beneficial features may be employed in embodiments alone or in combination with each other. The scope of the invention is thus indicated by the appended claims and all changes which come within the meaning and range of equivalency of the claims are therefore intended to be embraced.

What is claimed is:

1. An optical sensing system, comprising:
    a resonator arrangement comprising:
        a first resonator, wherein an effective refractive index of the first resonator is changeable in response to a change in a refractive index of a cladding of the first resonator; and
        a second resonator to which a current or voltage being adjustable in response to a change in the effective refractive index of the first resonator is applied;
    wherein the optical sensing system is configured to determine the change in the effective refractive index of the first resonator based on a change in the current or voltage applied to the second resonator.

2. The optical sensing system of claim 1, wherein the second resonator comprises a thermal heater, and wherein the current or voltage being adjustable in response to a change in the effective refractive index of the first resonator is applied to the thermal heater.

3. The optical sensing system of claim 1, further comprising:
    an input optical waveguide configured to guide received light;
    wherein the resonator arrangement is coupled to the input optical waveguide to receive the light from the input optical waveguide.

4. The optical sensing system of claim 1, further comprising:

a coupling optical waveguide coupled between the first resonator and the second resonator, the coupling optical waveguide being configured to guide light received from the first resonator to the second resonator or from the second resonator to the first resonator.

5. The optical sensing system of claim 4, further comprising:
an input optical waveguide configured to guide received light, wherein the resonator arrangement is coupled to the input optical waveguide to receive the light from the input optical waveguide; and
an output optical waveguide coupled to the resonator arrangement, the output optical waveguide being configured to output light received from the resonator arrangement,
wherein the first resonator is coupled to the input optical waveguide and the coupling optical waveguide, and the second resonator is coupled to the output optical waveguide and the coupling optical waveguide.

6. The optical sensing system of claim 5,
wherein the first resonator has an input port coupled to the input optical waveguide and an output port coupled to the coupling optical waveguide, wherein the first resonator is configured to receive light from the input optical waveguide via the input port, direct the light to the output port, and transmit the light to the coupling optical waveguide via the output port.

7. The optical sensing system of claim 5,
wherein the second resonator has an input port coupled to the coupling optical waveguide and an output port coupled to the output optical waveguide, wherein the second resonator is configured to receive light from the coupling optical waveguide via the input port, direct light from the input port to the output port, and transmit the light to the output optical waveguide via the output port.

8. The optical sensing system of claim 4, further comprising:
an input optical waveguide configured to guide received light, wherein the resonator arrangement is coupled to the input optical waveguide to receive the light from the input optical waveguide; and
an output optical waveguide coupled to the resonator arrangement, the output optical waveguide being configured to output light received from the resonator arrangement,
wherein the second resonator is coupled to the input optical waveguide and the coupling optical waveguide, and the first resonator is coupled to the output optical waveguide and the coupling optical waveguide.

9. The optical sensing system of claim 8,
wherein the second resonator has an input port coupled to the input optical waveguide and an output port coupled to the coupling optical waveguide, wherein the second resonator is configured to receive light from the input optical waveguide via the input port, direct the light to the output port, and transmit the light to the coupling optical waveguide via the output port.

10. The optical sensing system of claim 8,
wherein the first resonator has an input port coupled to the coupling optical waveguide and an output port coupled to the output optical waveguide, wherein the first resonator is configured to receive light from the coupling optical waveguide via the input port, direct light from the input port to the output port, and transmit the light to the output optical waveguide via the output port.

11. The optical sensing system of claim 1, further comprising:
an output optical waveguide coupled to the resonator arrangement, the output optical waveguide being configured to output light received from the resonator arrangement.

12. The optical sensing system of claim 11, further comprising:
a detector coupled to the output optical waveguide,
wherein the detector is configured to receive light from the output optical waveguide.

13. The optical sensing system of claim 12,
wherein the detector is configured to measure an intensity of light received from the output optical waveguide.

14. The optical sensing system of claim 13,
wherein the intensity of light is maximum when an optical resonant frequency of the first resonator and an optical resonant frequency of the second resonator are aligned.

15. The optical sensing system of claim 14,
wherein the optical resonant frequency of the first resonator changes in response to the change in the effective refractive index of the first resonator.

16. The optical sensing system of claim 15,
wherein the optical sensing system is configured to change the current or voltage applied to the second resonator to align the optical resonant frequency of the second resonator with the changed optical resonant frequency of the first resonator such that the intensity of light measured by the detector is maximum.

17. The optical sensing system of claim 1,
wherein the first resonator and the second resonator are identical.

18. The optical sensing system of claim 17,
wherein the first resonator and the second resonator each comprises a closed loop.

19. The optical sensing system of claim 18,
wherein the closed loops are ring-shaped.

20. The optical sensing system of claim 1, further comprising:
a light source configured to provide light.

21. The optical sensing system of claim 20,
wherein the light source comprises a broadband light source.

* * * * *